United States Patent
LaVerne

[11] 3,974,830
[45] Aug. 17, 1976

[54] METHOD AND APPARATUS FOR CARBON DIOXIDE THERAPY (CDT) OF ADDICTONS

[76] Inventor: Albert A. LaVerne, 17 E. 82nd St., New York, N.Y. 10028

[22] Filed: Jan. 27, 1975

[21] Appl. No.: 544,320

[52] U.S. Cl................................. 128/212; 128/185
[51] Int. Cl.²......................................... A61M 16/00
[58] Field of Search............. 128/212, 145.5, 145.6, 128/145.8, 184, 185, 213, 215, 256, 207, 203, DIG. 17, 202, 209

[56] References Cited
UNITED STATES PATENTS

| | | | |
|---|---|---|---|
| 2,007,330 | 7/1935 | Hicks................................. | 128/202 |
| 3,513,843 | 5/1970 | Exler................................. | 128/202 |
| 3,870,072 | 3/1975 | Lindemann......................... | 128/184 |

FOREIGN PATENTS OR APPLICATIONS

| | | | |
|---|---|---|---|
| 137,902 | 1/1920 | United Kingdom................. | 128/212 |
| 317,213 | 8/1929 | United Kingdom................. | 128/212 |
| 5,447 | 3/1910 | United Kingdom................. | 128/212 |

Primary Examiner—Robert W. Michell
Assistant Examiner—Henry J. Recla
Attorney, Agent, or Firm—Darby & Darby

[57] ABSTRACT

Method and apparatus for a non-addictive therapy for addiction, includng heroin, methadone and alcohol; the patient briefly breathes heated gas containing 79–80% carbon dioxide delivered through a face mask not touching the patient's face, treatments for several weeks or less sufficing for detoxification and subsequently a cure.

13 Claims, 2 Drawing Figures

METHOD AND APPARATUS FOR CARBON DIOXIDE THERAPY (CDT) OF ADDICTONS

BACKGROUND OF THE INVENTION

The problems of addiction, caused by agents such as heroin, methadone or alcohol, in contemporary American society are well known and numerous. In addition to problems experienced by the individual addict, for example, physical problems caused by dietary deficiencies, emotional problems caused by inability to work or maintain stable family relationships, the addiction inflicts costs borne by the entire society in several forms, including crimes resulting from illegal attempts to obtain money needed to support the addiction and addiction caused absenteeism from work.

Treatment of these addictions leading to a permanent cure has heretofore been either ineffective or time-consuming and slow, as, for example, individual or group psychotherapy. Some types of treatment, such as methadone treatment of heroin addiction, have simply failed since methadone substitutes one drug for another. All types of treatment have high relapse percentages after cessation of therapy. For any type of treatment, it is desirable that the beneficial effects of the treatment last for a long time period and be easily achieved and maintained so that the entire treatment does not have to be repeated.

Treatment begins with detoxification of the addiction. The detoxification process is often painful and slow for addicts and the painfulness of the process often deters addicts from initiating a course of treatment leading to a complete cure. The effectiveness of any currently existing treatment program would thus be enhanced if a rapid and painless method were available to detoxify the addict and then continue treatment leading to a longer term cure of the addiction.

It is an object of the present invention to provide a drug-free method for treating addictions.

It is a further object of the present invention to provide such a method that is effective for a long time period.

It is a still further object of the present invention to provide such a method that is non-addictive.

It is another object of the present invention to provide a method for painlessly and rapidly detoxifying addicts.

It is yet another object of the present invention to provide apparatus for the treatment of addictions.

SUMMARY OF THE INVENTION

The present invention relates to a method of curing addictions and detoxifying addicts, including heroin, methadone and alcohol, in which the addict inhales carbon dioxide, typically 70–80% carbon dioxide with the remaining gas being oxygen, for a period typically between 30 and 120 seconds. A series of treatments, with decreasing frequency, is given over a period of time, sometimes as long as several months, with the latter treatments on an outpatient basis. Detoxification occurs rapidly and painlessly within several days and continued treatment effects a complete cure of the addiction. Prior to the inhalation of carbon dioxide, the addict or patient is medicated to reduce treatment anxiety and enhance therapeutic efficacy. Pure oxygen is then administered for several minutes. The addict rapidly and spontaneously returns to full consciousness after $CO_2$-$O_2$ administration. Spontaneous rapid exhalation (hyperventilation) of the carbon dioxide after treatment eliminates all the excess carbon dioxide within seconds as shown by blood studies, and the oxygen saturation curve remains high for many hours, so there is never any hypoxia or anoxia.

The carbon dioxide and oxygen are mixed in a container surrounded by an insulated heating element having a thermostatic control that permits heating the gases to a controlled temperature prior to delivery to the patient. The gases are delivered to the patient from a face mask that does not touch the patient's face and permits the patient to move away from the mask if he so desired. This type of mask reduces treatment anxiety.

Heating the carbon dioxide-oxygen mixture (1) makes it easier to breathe, (2) eliminates suffocation anxiety caused by unheated gases used in prior carbon dioxide therapy (CDT) treatments, (3) eliminates treatment anxiety, the most serious and persistent side effect of CDT (unheated gas), (4) increases the therapeutic effectiveness of the CDT. These clinical and therapeutic results are impossible to obtain with unheated gases Heated $O_2$ or $CO_2$-$O_2$ also have been formed to have more profound and lasting effects upon the body chemistry and are much more therapeutic than unheated gases.

CDT treatment according to the present invention also has been found to be effective in other illnesses as psychiatric and neurological such as mental, emotional psychosomatic disorders, headaches, neuroligical, post concussion syndromes, dyslexia, minimal brain damage, and for people without specific disease and who are normal.

CDT stabilizes body chemistry and normalizes brain circuits. CDT resets the master control centers such as the chemostat, thermostat, psychostat and other as yet unidentified control centers that appear to be located in the upper respiratory, olfactory and sinus areas.

For example, patients suffering from colds, acute and chronic sinus infections, rhinitis, other forms of allergic upper respiratory syndrome, immune disease, asthmatic disorders, obtain immediate relief by CDT and recovery. Their reticuloendothelial and immune systems are stabilized. It seems that the basic biological system of metabolic rhythms are reset to a healthier level. Patients appear to become rejuvenated in physiological, psychological, mental and emotional areas. Central nervous system, vascular, endocrine, stress systems (pituitary-adrenal) become more efficient, and productive. The repetitive use of CDT seems to enhance total body health. It slows down catabolic processes, builds up anabolic processes of metabolism. In effect, CDT deters the aging process and encourages longevity. These observations and conclusions are based upon numerous patients treated with CDT.

The scope of the invention will be more fully apparent from consideration of the following description of a preferred embodiment of the invention described with reference to the accompanying drawings in which:

DESCRIPTION OF THE PREFERRED EMBODIMENT

Figure 1:
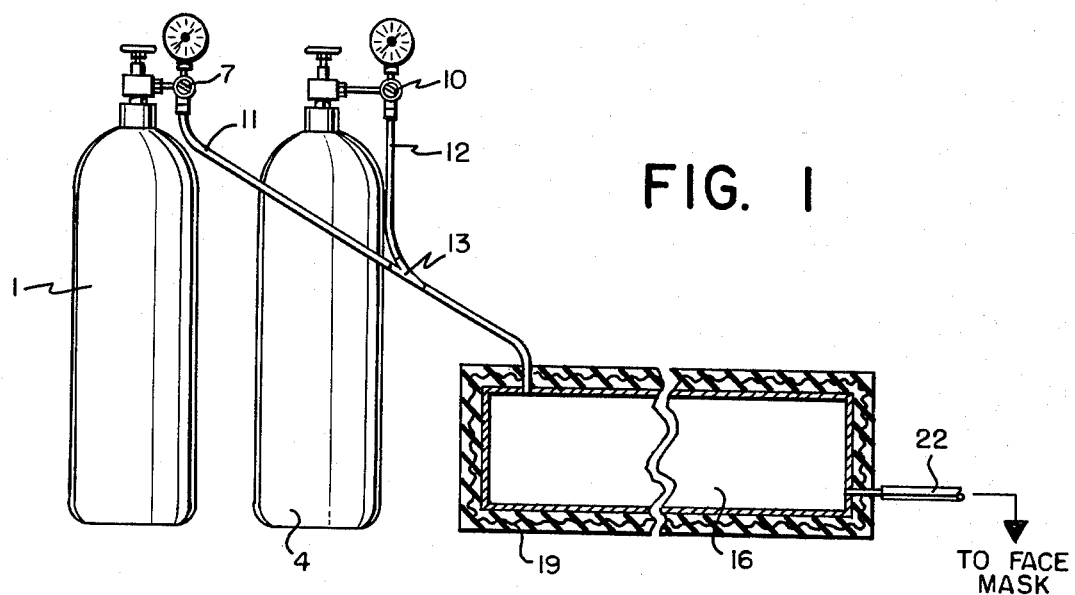
FIG. 1 is a schematic representation of the treatment apparatus.

Carbon dioxide is stored in tank 1 and oxygen in tank 4. Both gases are stored under pressure. The gas flow from tanks 1 and 4 is controlled by regulator valves 7 and 10, on tanks 1 and 4, respectively. Any suitable tanks and valves may be used, but the valves must be adjustable to yield the desired flow rate and mixture described below. Two pieces of tubing 11 and 12 have, in a preferred embodiment, one end each connected to regulator valves 7 and 10, respectively, and the other ends connected to one branch each of Y-connector 13. The remaining branch of Y-connector 13, that is, the branch of Y-connector 13 not connected to either tubing 11 or 12 feeds into a container 16, which, in a preferred embodiment, is surrounded by an insulated heating element 19 having a thermostatic control (not shown) to permit accurate temperature regulation of the interior of container 16. Container 16 must be large enough to permit thorough mixing of the oxygen and carbon dioxide. An exit tube 22 leads from container 16 to face mask 25. A breathing bag may be attached to exit tube 22. To facilitate placement of mask 25, tube 22 should be flexible. The entire system should be air-tight to prevent leakage of either carbon dioxide or oxygen which might cause a fire hazard.

Since the gases are heated, all tubing and connections should be heat resistant. The entire system should be thermally insulated and spark free to reduce fire hazards. The carbon dioxide may contain water or other impurities that cause icing within the regulator valve 7 as a result of cooling caused by the rapid expansion of the gas upon leaving tank 1. To insure a steady flow of carbon dioxide, a heating unit (not shown) may be placed between the carbon dioxide tank 1 and the regulator valve 7 to warm the gas.

In a preferred embodiment, face mask 25 is made from a transparent material and has a generally bowl-shaped form. Exit tube 22 delivers the gas mixture to the bottom of the bowl. Tube 22 is securely connected to port 26, which extends outwardly from the bottom of mask 25, by any suitable airtight means, such as a clamp 27. The inner surface of mask 25 is covered with a diffusing plate 28 which can be several layers of a fine wire screen or perforated plastic. Diffusing plate 28 diffuses the gas flow over the entire open area of top of mask 25. Any suitable diffusing means may be used. Face mask 25 does not have a rubber face cushion around the top as it normally does not touch the patient's face during inhalation.

PREMEDICATION

Some premedication is normally administered to the patient to allay anxiety, prevent excessive autonomic reactions and eliminate vitamin deficiencies normally found in addicts. The premedication renders the treatment more effective. Typical medication give to patients includes phenobarbital — 100 mg, atropine — 10 mg, ascorbic acid — 1000 mg, and Vitamin E — 600 I.U., propranolol 10 to 40 mg, dexamethasone 1 to 3 mg, and is administered about 1 hour prior to the carbon dioxide treatment. Other medication may be administered to deal with problems specific to individual patients.

TREATMENT PROCEDURE

Figure 2:
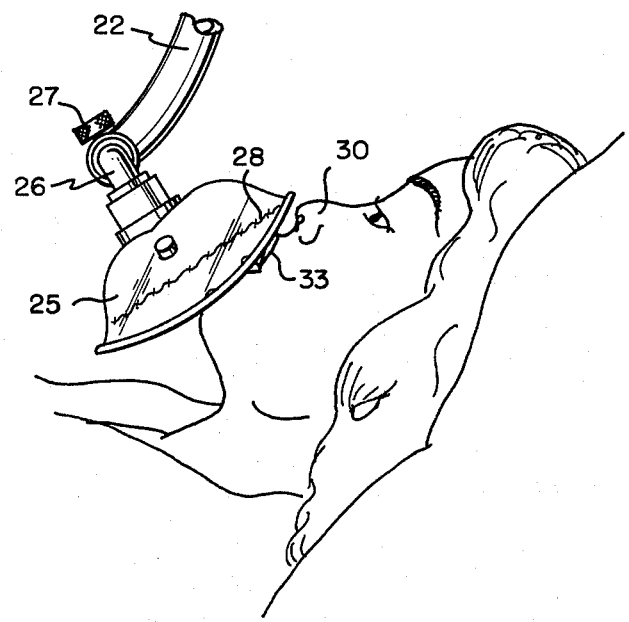
FIG. 2 shows the position of the face mask with respect to the face of a patient.

The position of mask 25 and the velocity of the gas exiting from mask 25 have been found to be important variables in the effectiveness of the treatment. The preferred position of mask 25 with respepct to the patient's face is shown in FIG. 2. Either mask 25 or tube 22 is held so that the edge of mask 25 is indirectly over the nose 30 and mask 25 covers the mouth 33. Since mask 25 does not touch the face, the patient can breathe easily through both nose and mouth without any suffocation anxiety. Although carbon dioxide is normally difficult to breathe, this technique enables the patient to inhale more carbon dioxide and permits reaching of the therapeutic end point (described below) with hyperventilation but without loss of consciousness. The stream of gas from mask 25 is controlled with valves 7 and 10 until it is gentle but yet strong enough to convey the gas to the mouth 33 and nose 30 without dilution by the ambient air. This technique is called the Rapid Non-Coma technique with coma understood as meaning a state of altered consciousness rather than a profound or irreversible stupor without voluntary activity.

The carbon dioxide and oxygen are heated in container 16 by heating element 19 to a temperature between 90° and 130°F with the average temperature used being 104°F. The thermostatic control permits the temperature to be regulated and maintained accurately in the desired range. It is found that heating has two beneficial effects. The increased kinetic energy imparted to the gas molecules by heating results in more effective chemical and physiological therapeutic effects on the body tissues than is normally achieved with cold gases. The transition from the initially pure oxygen to an oxygen-carbon dioxide mixture is less noticed by the patient because the pungent odor and irritating effects on mucous membranes caused by the gases are reduced in comparison with room temperature or chilled gases.

The patient is initially administered 5 to 10 minutes of pure oxygen. The delivery of the gas mixture is then adjusted by valves 7 and 10 and set so that the patient is given a mixture that is usually 70–80% carbon dioxide and 20–30% oxygen. The delivery rate of the mixture is controlled so that it is a gentle stream. It has been found that both the optimum gas temperature and optimum ratio of carbon dioxide to oxygen vary among different patients and the addiction treated and must be individually determined. Some patients may be better treated with unheated air. The number of breaths administered until the therapeutic end point (described below) is reached varies between 10 to 80. Shallow breathers generally require more breaths than deep breathers. Thirty breaths are typical. Since mask 25 does not touch the face of the patient, the patient may move away from the mask 25 at any time. This results in lessened treatment anxiety and increased confidence in the treatment and the therapist.

A modified Rapid Non-Coma technique of administering carbon dioxide has been found effective and is preferred by some patients. The mask 25 is positioned directly over the patient's nose and mouth but without touching the face and 5–15 deep breaths of the oxygen-carbon dioxide mixture, fewer for a heated mixture, administered. This is an effective dose that does not produce unconsciousness. Two to eight such treatments per day produce good results without any treatment anxiety.

A simple procedure is followed to determine the therapeutic end point and thus, the number of breaths of carbon dioxide administered. The patient is asked to raise right and left arms alternately at 5 second intervals during the period of carbon dioxide inhalation. The degree and speed of response indicate the patient's state of consciousness. No response or a minimal response indicates that the therapeutic end point has been reached. Patient spontaneously returns to full consciousness in seconds. Valves 7 and 10 are again adjusted to administer post treatment pure oxygen (or use of separate heated $O_2$ tank supply) for 1–3 minutes.

To enable the person administering the treatment to observe a new patient's tolerance and sensitivity to carbon dioxide, it is desirable to first give the patient about five carbon dioxide-oxygen breaths, with increments of two breaths during subsequent treatments.

The treatment room should be provided with an adequate ventilation system to prevent carbon dioxide from building up to a potentially toxic level in the ambient air.

It has been found that precise carbon dioxide-oxygen ratios are more easily maintained if carbon dioxide tank 1 is replaced by a new tank when the regulator valve 7 pressure has dropped from its valve for a full tank of 950 lbs. to 750 lbs. or less.

Treatment frequency gradually decreases. The treatments are given daily initially, with one to eight treatments for 2 to 4 days depending upon the patient and addiction, then one treatment daily up to 2 weeks, then three times a week for a month and weekly treatments for another month followed by discharge. The daily treatments may be given on an in-patient basis with the latter treatments on an out-patient basis. Initiation of treatment is usually followed by a rapid loss of desire for drugs. Detoxification normally occurs in less than 1 week.

MECHANISM OF ACTION

Although high carbon dioxide levels relieve the symptoms of addiction, the details of the operative mechanisms are not known although the effect of carbon dioxide on the central nervous system is probably involved.

The physiological objective of the therapy is to rapidly increase the carbon dioxide level in the brain and produce alterations in the brain chemistry and circuits leading to clinical recovery from the addiction. The high and sudden concentrations of carbon dioxide induce an intense adaptive stress reaction. The rapid change minimizes the ability of the body and brain to resist chemical, neuronal and circuit changes. The adaptive stress reaction tends to correct the endocrinological system. The repetitive treatments condition the organs and systems involved to function more effectively and bring about a clinical frequently permanent remission of the addiction symptoms.

The clinical manifestations of narcotic withdrawal suggest a centrally mediated autonomic hyperexcitability. It is thus plausible to hypothesize that high concentrations of carbon dioxide used in the treatment suppress the central autonomic and hypothalamic centers and result in an amelioration of the narcotic withdrawal symptoms.

The high carbon dioxide concentrations also renders the brain susceptible to physical or psychological stimuli. Any resulting alterations in the brain are long lasting rather than transient. Consequently, administration of any unpleasant stimuli to the patient during the treatment process may create undesirable negative responses that retard recovery and should be avoided.

Clinical experience shows that carbon dioxide therapy is non-addictive and does not dull the patient's mental processes. Nor does it slow down the patient as do central nervous system depressants such as methadone. Clinical results also show that addicts lose their desire for heroin or methadone soon after the treatments begin and many also show renewed interest in their families. Most patients become cooperative and often look forward to future treatments.

Although high concentrations of carbon dioxide without available oxygen can be toxic, the method of treatment described is completely safe. For death to occur from carbon dioxide poisoning, the carbon dioxide concentration must be both high and prolonged and must produce anoxia or severe hypoxia. The CDT carbon dioxide concentration used is high but available oxygen 20 to 30% is always breathed by the patient. This cannot cause death as all the excess carbon dioxide is expelled within 30 seconds after inhalation ceases and the $CO_2$ inhalation is never prolonged. Rather CDT is an acute exposure of short duration, non-toxic and therapeutic.

Administration of carbon dioxide soon after general anesthetics have been administered may be dangerous. However the method of CDT and premedication herein described is perfectly safe.

CLINICAL RESULTS

An experimental clinical study of the effectiveness of carbon dioxide therapy has been performed with 42 patients, nine lost to follow-up studies, who stayed for 1 week of hospitalization and were then released for out-patient treatment. Of the heroin and methadone addicts, 4 months after the end of the hospitalization, 33% were narcotics free 100% of the time, 39% were narcotics free 60% of the time and 27% were narcotics free less than 60% of the time. Of eight alcoholics in the study, three were followed for 6 months and remained alcohol free.

The detoxification process of the subject invention is painless and rapid. Heroin addicts are typically detoxified in 2 to 4 days and methadone addicts in 5 to 10 days. This rapid detoxification makes carbon dioxide therapy useful in conjunction with other treatment programs such as methadone maintenance or group therapy sessions. Carbon dioxide treatments have also been found successful in curtailing the rehabilitation time needed by other programs.

Although a preferred embodiment of the invention has been described, it is to be understood that this disclosure is for the purposes of illustration only and certain modifications may be obvious to those skilled in the art, for example, the carbon dioxide and oxygen may be heated at any point after leaving the tanks rather than in the container, and that as a result the scope of the invention is to be determined by reference to the following claims.

What is claimed is:

1. A method of treating addictions in human patients by carbon dioxide therapy comprising the steps of:
    providing a mixture of carbon dioxide and oxygen gases in which the major portion of the gas mixture is carbon dioxide, heating the gas mixture, and administering the heated gas mixture for breathing by the patient in an amount sufficient to reduce the state of consciousness in the patient to a state less than a full coma.

2. A method as in claim 1 wherein the carbon dioxide comprises in the range of between about 70%–80% of the mixture and the balance of the mixture is substantially oxygen.

3. A method as in claim 1 further comprising the step of controlling the temperature of the heated gas mixture administered to the patient to within a predetermined range.

4. A method as in claim 1 wherein the gas mixture is heated to a temperature in the range of from about 90°F to about 130°F.

5. A method as in claim 1 further comprising the step of controlling the rate at which the gas mixture is administered to the patient to thereby administer a quantity of gas which is tolerable to the patient.

6. A method as in claim 5 wherein the carbon dioxide comprises in the range of between about 70%–80% of the mixture and the balance of the mixture is substantially oxygen.

7. A method as in claim 1 further comprising the step of medicating the patient with a sedative to reduce anxiety before administering the gas mixture.

8. A method as in claim 1 further comprising the step of adjusting the ratio of the gases in the carbon dioxide oxygen mixture administered to the patient to obtain best clinical results, with the major portion of the adjusted ratio still comprising carbon dioxide.

9. A method as in claim 1 further comprising the step of administering oxygen without carbon dioxide to the patient immediately prior to the step of administering the gas mixture.

10. A method as in claim 1 further comprising the step of administering oxygen to the patient after the patient has spontaneously returned to consciousness.

11. A method as in claim 1 wherein the step of administering the gas mixture comprises:

providing a face mask to which the gas mixture is supplied, and placing the face mask adjacent the face of the patient but out of contact with the face so that the patient can easily move away from the mask.

12. A method as in claim 11 further comprising the step of diffusing the gas in the face mask.

13. A method of treating addictions in human patients by carbon dioxide therapy comprising the steps of:

providing a mixture of carbon dioxide and oxygen gases wherein the major portion of the gas mixture is carbon dioxide, administering the mixture to a patient for breathing through a face mask which is placed adjacent to but out of contact with the face of the patient so that the patient can move away from the mask in an amount sufficient to reduce the state of consciousness in the patient to a state less than a full coma.

* * * * *